(12) United States Patent
Wilbertz et al.

(10) Patent No.: US 7,918,123 B2
(45) Date of Patent: Apr. 5, 2011

(54) GAS SENSOR

(75) Inventors: Christoph Wilbertz, Gundelfingen (DE); Heinz-Peter Frerichs, St. Peter (DE)

(73) Assignee: Micronas GmbH, Freiburg i.Br. (DE)

( * ) Notice: Subject to any disclaimer, the term of this patent is extended or adjusted under 35 U.S.C. 154(b) by 462 days.

(21) Appl. No.: 12/142,292

(22) Filed: Jun. 19, 2008

(65) Prior Publication Data

US 2009/0078026 A1    Mar. 26, 2009

(30) Foreign Application Priority Data

Jun. 22, 2007    (EP) .................................... 07012222

(51) Int. Cl.
*G01N 9/00* (2006.01)

(52) U.S. Cl. ......................................... 73/31.06; 73/23.2

(58) Field of Classification Search .................. 73/31.06, 73/23.2

See application file for complete search history.

(56) References Cited

U.S. PATENT DOCUMENTS

| | | | | |
|---|---|---|---|---|
| 5,779,980 A | * | 7/1998 | Hatfield ........................... | 422/95 |
| 6,155,100 A | | 12/2000 | Stokes et al. | |
| 6,196,052 B1 | * | 3/2001 | May et al. ..................... | 73/24.06 |
| 7,538,400 B2 | * | 5/2009 | Segal et al. .................... | 257/414 |
| 2007/0108068 A1 | * | 5/2007 | Suh et al. ....................... | 205/766 |

FOREIGN PATENT DOCUMENTS

| | | |
|---|---|---|
| DE | 4333875 A1 | 4/1995 |
| DE | 4333875 C2 | 8/1995 |
| DE | 10118366 A1 | 10/2002 |
| DE | 10161214 A1 | 7/2003 |

OTHER PUBLICATIONS

Jeyaprakash J.D. et al. "A Simple Route Towards the Reduction of Surface Conductivity in Gas Sensor Devices," Sensors and Actuators B,Oct. 2005, pp. 218-224, Bd. 110 Nr. 2, Elsevier Sequoia S.A.
Flietner B. et al."Reliable Hybrid GasFETs for Work-Function Measurements with Arbitrary Materials," Sensors and Actuators B, Nov. 1994, pp. 109-113 Bd. 110 Nr. 2, Elsevier Sequoia S.A.

* cited by examiner

*Primary Examiner* — Hezron Williams
*Assistant Examiner* — Rodney T Frank
(74) *Attorney, Agent, or Firm* — Muncy, Geissler, Olds & Lowe, PLLC

(57) ABSTRACT

A gas sensor has at least one gas sensitive layer, which has at least one surface area in which the work function is dependent upon the concentration of a target gas capable of being brought into contact with the surface zone. At least one electric potential sensor is capacitatively coupled to the surface zone over an air gap. The surface zone of the gas sensitive layer is covered with an electrically insulating coating which is inert to the target gas and which is adhesively bound to the gas sensitive layer. The coating is configured so that it is permeable to the target gas and so that when the target gas contacts the surface zone of the gas sensitive layer, it prevents or at least impedes an alteration of the bound state of atoms and/or molecules bound to the surface zone and differing from the target gas.

10 Claims, 6 Drawing Sheets

GAS SENSOR

Figure 1:
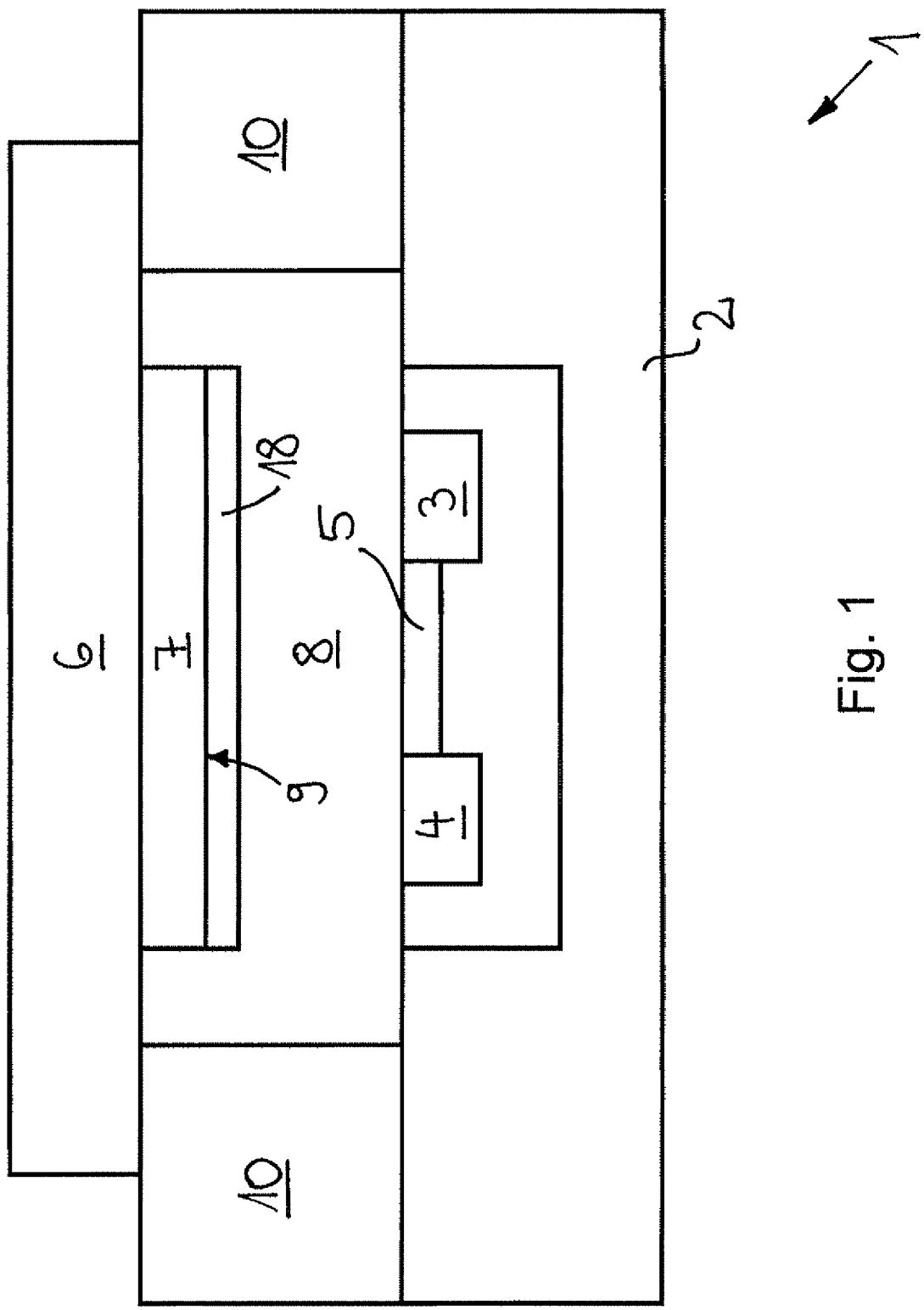

The invention relates to a gas sensor with at least one gas sensitive layer having at least one surface zone in which the work function is dependent upon the concentration of a target gas capable of being brought into contact with the surface zone, and with at least one electric potential sensor capacitatively coupled to the surface zone over an air gap.

A gas sensor of this nature is disclosed in DE 43 33 875 C2. The gas sensor has a silicon substrate in which a field-effect transistor is integrated. The field-effect transistor has a gate electrode, which is conductively connected with a sensor electrode, over which a gas sensitive layer is arranged, said layer being separated from the sensor electrode by an air gap and capacitatively coupled to the sensor electrode by means of the air gap. A cover electrode is attached to the backside of the gas sensitive layer facing away from the sensor electrode. A surface zone of the gas sensitive layer facing the sensor electrode is capable of being brought into contact with a target gas, which upon contacting the surface zone is adsorbed thereon. The work function in the surface zone of the gas sensitive layer changes as a function of a change in the concentration of the target gas. Because the sensor electrode is capacitatively coupled to the surface zone, the electric potential on the gate electrode also changes. The current flow between a drain connection and a source connection of the field-effect transistor is controlled as a function of the change in potential. With certain gas sensitive layer and target gas combinations, the gas sensor may be disadvantageous in that the measurement signal of the field-effect transistor is strongly non-linear. As can be discerned in FIG. 6, the measurement signal (M), for example, initially diminishes relatively rapidly in the event of an abrupt increase of the concentration (K) of the target gas, afterwards increasing again and surpassing the level which it had prior to the increase in the concentration. Subsequently, a more gradual diminishment of the measurement signal initially takes place, followed by a renewed increase and finally another diminishment of the measurement signal. Analysis of the measurement signal of the gas sensor is therefore relatively difficult.

The object of the invention is therefore to create a gas sensor of the aforementioned type in which the measurement signal essentially corresponds to the change of the target gas concentration.

This object is achieved according to the invention in that the surface zone of the gas sensitive layer is covered with an electrically insulating coating which is inert to the target gas and which is adhesively bound to the gas sensitive layer and configured so that it is permeable to the target gas and further configured so that it prevents or at least impedes a change of the bound state of atoms and/or molecules bound to the surface zone and differing from the target gas when the latter contacts the surface zone of the gas sensitive layer.

The invention is based on the finding that an adsorption of the target gas takes place on the surface zone of the gas sensitive layer in an uncoated gas sensitive layer in the presence of an increase of the concentration of the target gas and that furthermore, during the change in surface work function thus induced, the surface zone of the gas sensitive layer can be altered by the target gas, for example, by chemical reactions on the surface or by the target gas displacing other atoms and/or molecules bound to the surface of the gas sensitive layer as it is adsorbed on the surface. As a consequence of these effects, the work function can change in the direction opposite to the adsorption-induced alteration. Depending on the temperature of the gas sensitive layer, the alteration of the surface can take place over hours (e.g., at room temperature) or seconds (e.g., at 70° C.) and thus strongly interfere with the adsorption-generated measurement signal. This interference occurs especially if the surface zone of the gas sensitive layer has not been in contact with the target gas for a prolonged period.

Surprisingly, the interference signal generated by the alteration of the surface zone can be reduced or even completely suppressed by the coating of the invention applied to the gas sensitive layer. Analogously, the interference single is also compensated, at least partially, by the coating in the event of a decrease in the target gas concentration. The coating thus acts as a passivation layer, which stabilizes the surface zone of the gas sensitive layer. The measurement signal of the gas sensor is thus considerably easier to analyze than would be the case for an otherwise equivalent gas sensor lacking the coating. An electrically insulating coating is to be understood as a coating the electrical whose conductivity is sufficiently low so that the coating does not form an equipotential surface that screens the gas sensitive layer from the air gap.

In a preferred embodiment of the invention, the coating is configured so that it prevents or at least impedes the binding of an electronegative gas differing from the target gas, especially of oxygen, on the surface zone of the gas sensitive layer. The surface zone of the gas sensitive layer provided for adsorption of the gas to be detected can then be stabilized by means of the coating, especially against the penetration of atmospheric oxygen. Preference is given to application of the coating to the gas sensitive layer during or immediately after the manufacture of the latter, so that the gas sensitive layer is protected from the outset from atmospheric oxygen and thus from an alteration of the oxidation state of its surface.

The coating is advantageously a monomolecular layer. The target gas can then penetrate the coating and reach the surface of the gas sensitive layer especially well.

It is advantageous if the coating contains a silane, in particular a silane in which a silicon atom is bound to at least one electronegative gas atom, preferably chlorine. The coating will then adhere well to the surface of the gas sensitive layer so that the latter is permanently passivated. Preference is given to wet chemical application of the silane to the gas sensitive layer for producing the coating. The silane preferably has at least one organic group and is especially an organotrichlorosilane.

Preference is given to the silane having at least one organic residual group. The residual group facilitates the application of the coating to the gas sensitive layer during the manufacture of the gas sensor in that the silane is applied, for example, in liquid form to the coating by means of, for example, a wet chemical immersion method.

In a preferred embodiment of the invention, the gas sensitive layer is composed of platinum or palladium. The gas sensor then has a high detection sensitivity for the target gas hydrogen.

In another preferred embodiment of the invention, the gas sensitive layer is an organic layer. The gas sensor can then be economically manufactured.

Preference is given to the potential sensor being a field-effect transistor comprising a substrate on which a drain and a source are arranged, wherein a channel zone is formed between the drain and source, and wherein the channel zone is capacitatively coupled to the surface zone of the gas sensitive layer directly over the air gap or indirectly by means of a gate electrode, which is coactive with the channel zone, and a sensor electrode, which is conductively connected to the gate electrode. The field-effect transistor can thus be an SGFET or a CCFET. The gas sensor thus enables a compact configuration and furthermore is easily integrated in a semiconductor chip. An analysis mechanism for processing the measurement signals of the gas sensor can also be integrated in the semiconductor chip.

In another advantageous embodiment of the invention, the gas sensor is configured as a Kelvin probe, in which the potential sensor is capacitatively coupled to the surface zone of the gas sensitive layer via an electrode which is separated from the surface zone of the gas sensitive layer by the air gap and displaceable toward and away from the surface zone of the gas sensitive layer. The electrode is thus capable of being positioned relative to the gas sensitive layer and brought into oscillation by means of, for example, a piezo actuator. The potential sensor is allocated to an evaluator and control mechanism, which induces a countervoltage on the electrode, which is selected so that the potential measured by the potential sensor is equal to zero at the center. The countervoltage is a measurement for the concentration of the target gas in contact with the surface zone of the gas sensitive layer.

Figure 2:
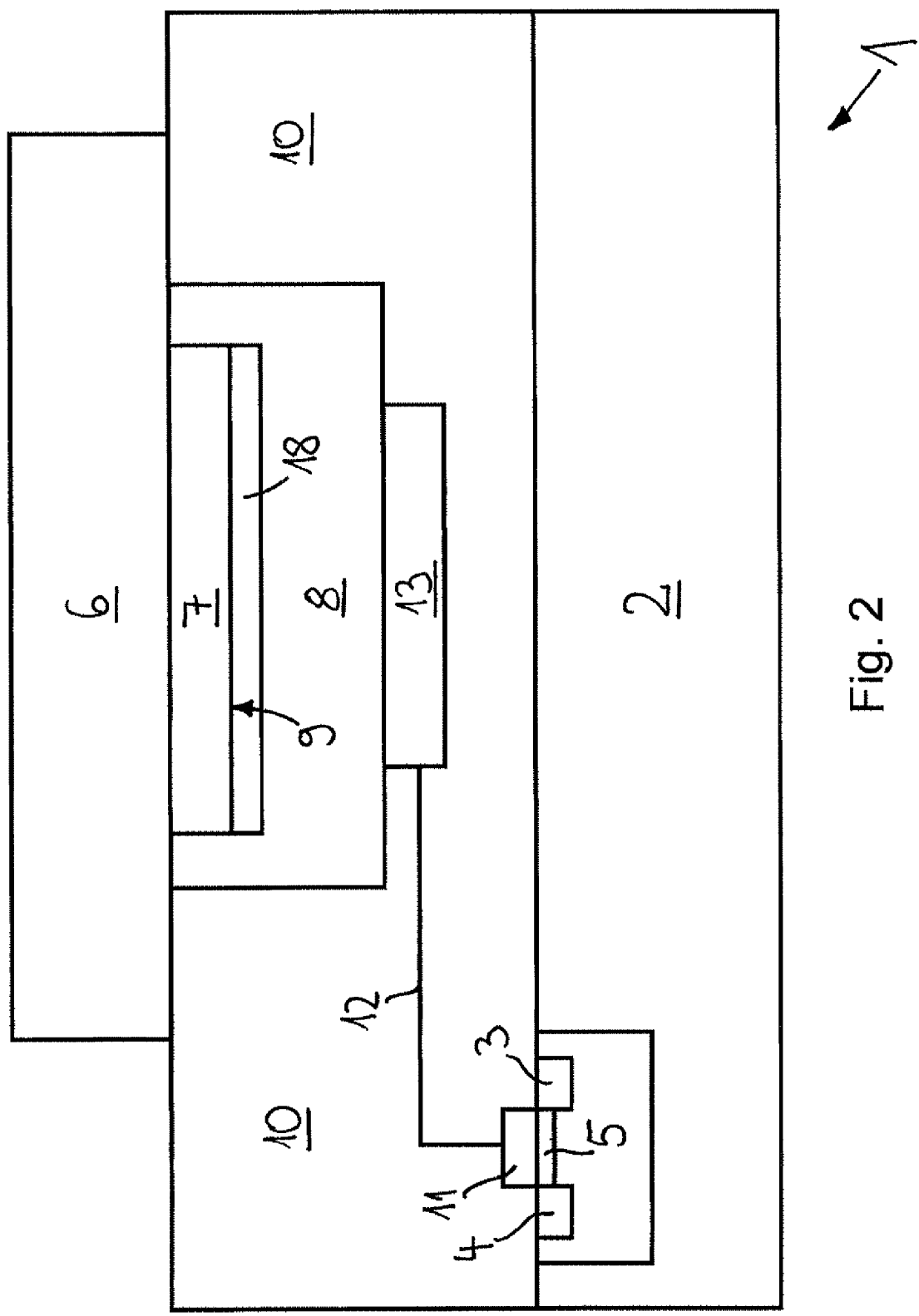
Figure 3:
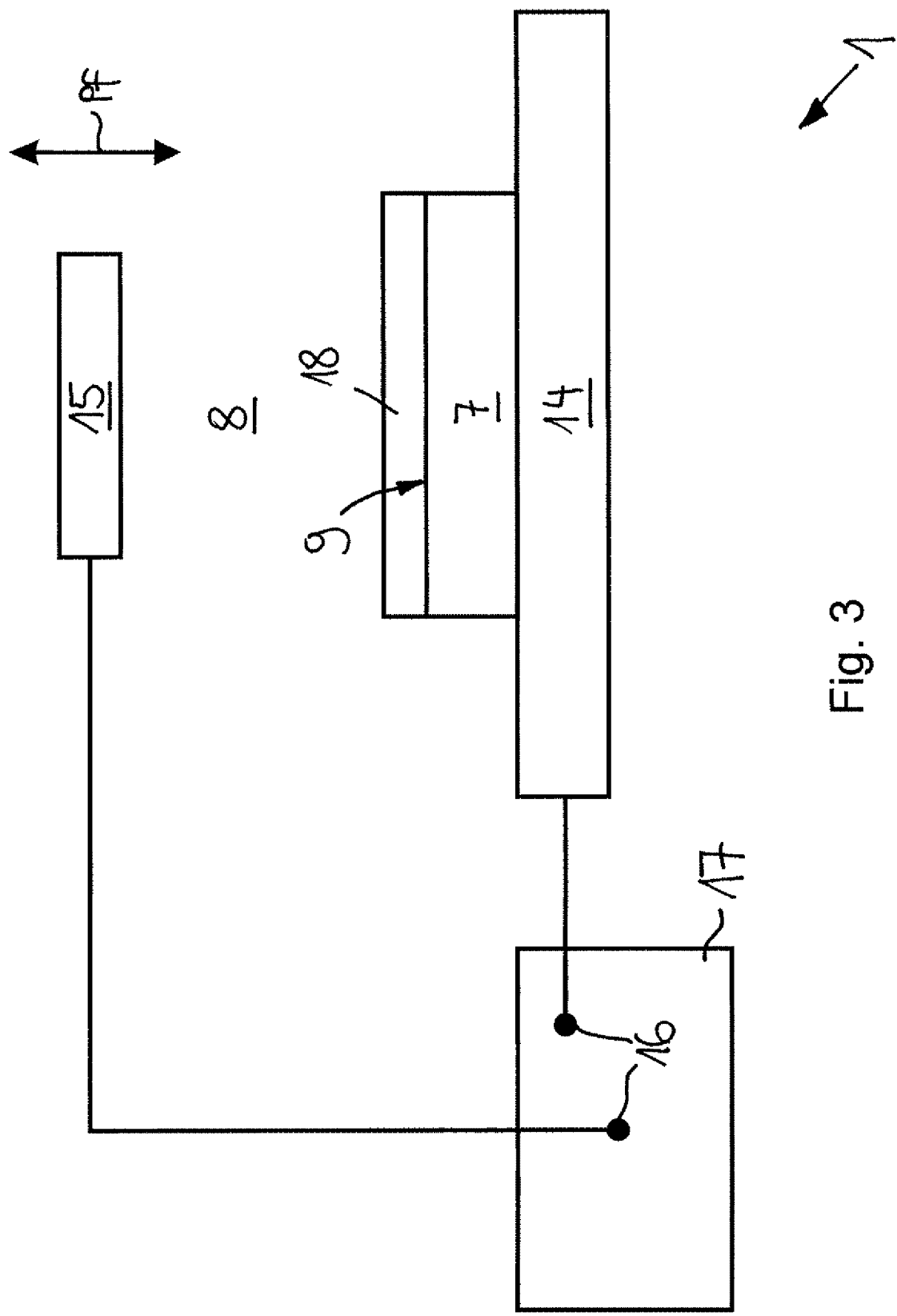
Figure 4:
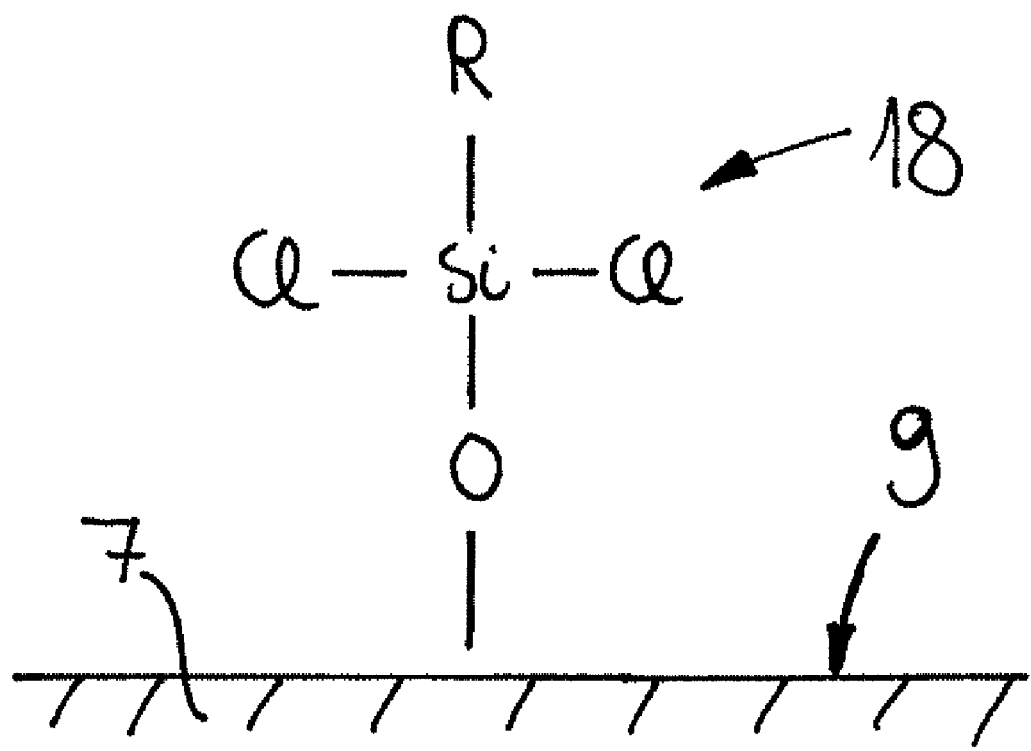
Figure 5:
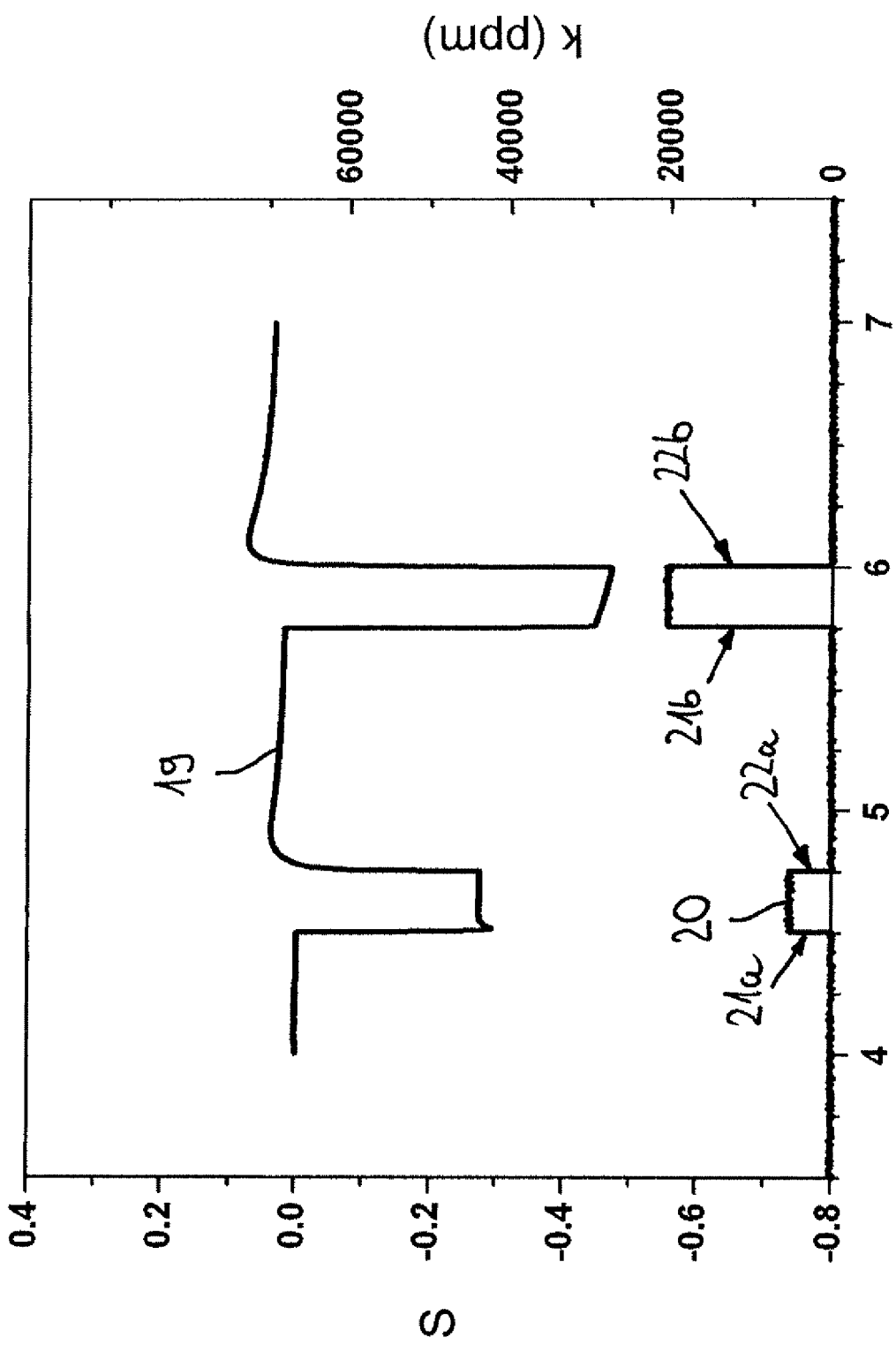
Figure 6:
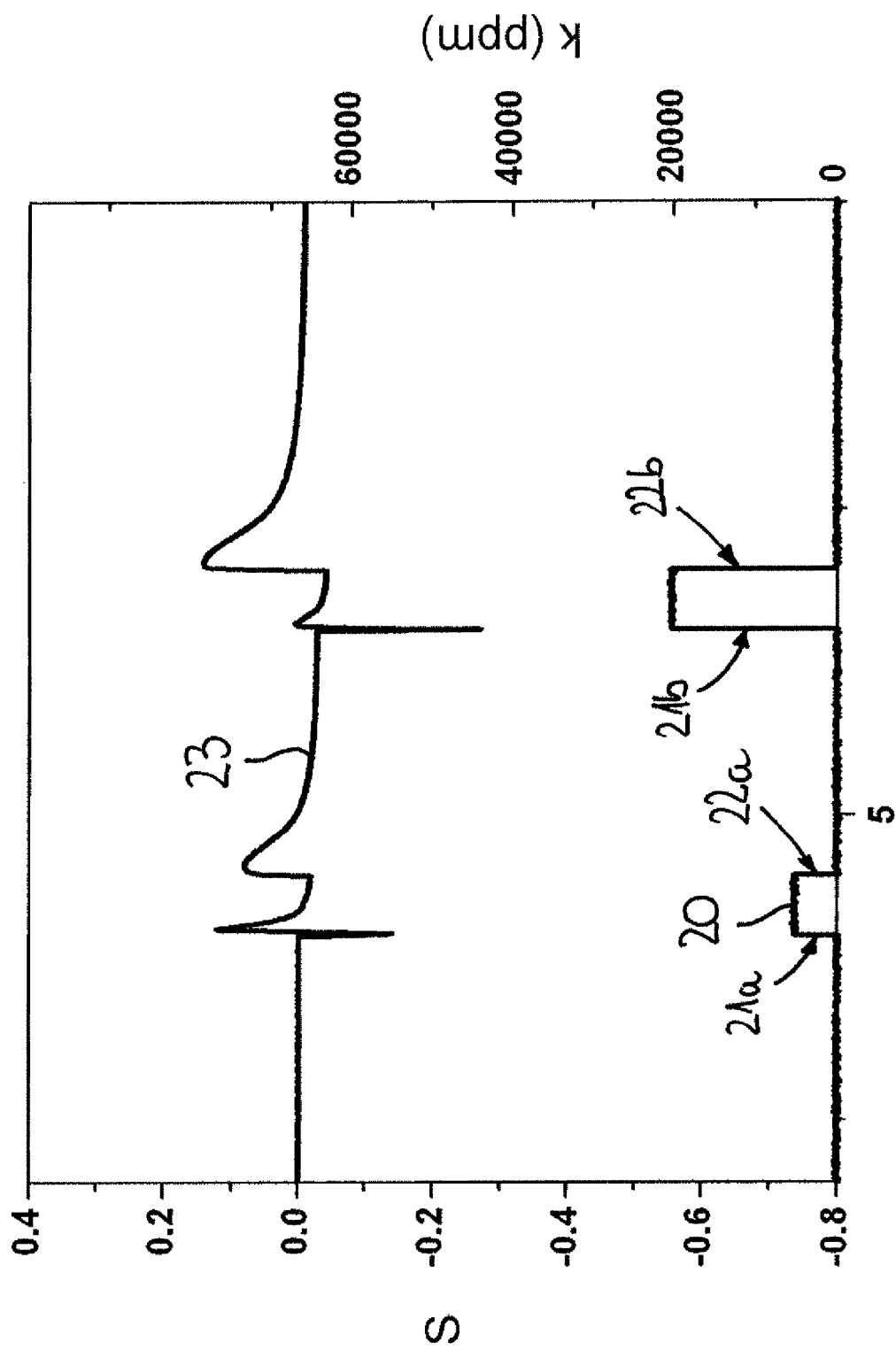

Illustrative embodiments of the invention are explained in more detail in the following, with reference to the drawing. Shown are:

FIG. 1 a cross-section of a gas sensor having an SGFET the channel zone of which is capacitatively coupled over an air gap to a gas sensitive layer with a passivation coating, FIG. 2 a cross-section of a gas sensor having an CCFET the sensor electrode of which is capacitatively coupled over an air gap to a gas sensitive layer with a passivation coating, FIG. 3 a cross-section of a gas sensor configured as a Kelvin probe, in which the gas sensitive layer has a passivation coating, FIG. 4 a schematic illustration of a silane molecule contained in the coating, which is bound to the gas sensitive layer by an oxygen bridge, FIG. 5 a graphic illustration of the measurement signal (top curve) and the target gas concentration (bottom curve) of a gas sensor, in which the gas sensitive layer has the coating of the invention, wherein the time t is plotted on the abscissa, and the amplitude S of the measurement signal and the target gas concentration k are plotted on the left and right of the ordinate, respectively, and FIG. 6 a graphic illustration similar to FIG. 5 in which, however, the measurement signal was measured with a prior art hydrogen sensor with an uncoated gas sensitive layer.

A gas sensor designated in its entirety by 1 in FIG. 1 has a substrate 2 on which a drain 3 and a source 4 are arranged in an n-doped tub of a transistor. The drain 3 and the source 4 can consist of, for example, p-doped silicon. The drain 3 is connected via electrical conductor paths to a drain connection, which is not illustrated in any greater detail in the drawing. The source 4 is connected to a source connection in an analogous manner. A channel zone 5 with a thin layer of oxide insulation acting as a gate dielectric arranged thereon is formed in the substrate 2 between the drain 3 and the source 4.

A gas sensitive layer 7, which is composed of, for example, a noble metal, especially platinum or palladium, and which is separated from the channel zone 5 by an air gap 8, is arranged on a bearing element 6 over the channel zone 5. A surface zone 9 of the gas sensitive layer 7 faces the channel zone 5 and is capacitatively coupled over the air gap 8 to the channel zone 5.

The bearing element 6 is connected to the substrate 2 on both sides of the gas sensitive layer 7 via an electrical insulation layer 10. It can be clearly discerned in FIG. 1 that the bearing element 6 and the gas sensitive layer 7 form a suspended gate.

The air gap 8 is connected with the atmosphere surrounding the gas sensor 1 via at least one opening, which is not shown in any greater detail in the drawing. The surface zone 9 of the gas sensitive layer 7 can be brought into contact via this opening with a target gas to be detected, namely hydrogen. Upon contact with the surface zone 9 the target gas is adsorbed on said surface zone 9. The work function is thus altered in the surface zone 9, which induces an alteration in the electric potential in the channel zone 5.

In the illustrative embodiment of FIG. 1, the channel zone 5 is openly configured (ISFET) and capacitatively coupled directly to the gas sensitive layer 7 by means of the thin oxide layer and the air gap 8. It can be clearly discerned that the channel zone 5 is arranged on the side of the air gap 8 opposite the gas sensitive layer 7.

In the illustrative embodiment of FIG. 2, the field-effect transistor is configured as an SGFET in which the channel zone 5 is laterally arranged next to the gas sensitive layer 7 in the substrate 2 and covered with a gate electrode 11. For the capacitative coupling of the channel zone 5 to the gas sensitive layer 7, the gate electrode 11 is connected via an electrical connecting line 12 to a sensor electrode 13, which is arranged on the side of the air gap 8 opposite the surface zone 9 of the gas sensitive layer 7 on an insulation layer 10 located on the substrate 2. The insulation layer 10 can be, for example, an $SiO_2$ layer. The structure of the suspended gate of the SGFET is analogous to that of FIG. 1.

In the illustrative embodiment shown in FIG. 3, the gas sensor 1 is configured as a Kelvin probe. The gas sensitive layer 7 is arranged on an electrically conductive support 14 and on its side facing away from said support 14 it has a surface zone 9 on which the target gas is capable of being adsorbed. The surface zone 9 is spaced from an electrode 15 by an air gap 8 and forms an electric capacity with said electrode 15.

The electrode 15 can be brought into oscillation by means of an actuator, which is not shown in any greater detail in the drawing. The electrode 15 oscillates toward and away from the gas sensitive layer 7 as indicated by the arrow Pf. The electrode 15 and the support 14 or the gas sensitive layer 7 are connected to terminals 16 of an evaluator and control mechanism 17. Said mechanism 17 has a potential sensor which is not shown in any greater detail in the drawing and which is connected to the terminals 16 in order to measure the voltage between the gas sensitive layer 7 and the electrode 15. Furthermore, the evaluator and control mechanism 17 has an adjustable voltage source control-connected to the potential sensor, by means of which a countervoltage is induced between the potential sensor and the electrode 15 and/or the support 14. The countervoltage is selected so that the potential measured by the potential sensor is equal to zero in the center.

In the previously described illustrative embodiments of the gas sensor 1, the surface zone 9 of the gas sensitive layer 7 is always covered with a electrically insulating coating 18 which is inert to the target gas. As can be discerned in FIG. 4, the coating 18 is a monomolecular layer composed of silanes, which are bound via oxygen bridges to the surface zone 9 of the gas sensitive layer 7 and adhere thereto. The silanes have an organic residual group, which is designated by R in FIG. 4.

The coating 18 is permeable to the target gas. The coating 18 prevents or impedes a chemical reaction of the target gas with the surface 9, for example with the oxygen residing on the surface 9. The coating 18 prevents or impedes the oxygen contained in the air surrounding the gas sensitive layer 7 from reacting with or bonding to the surface zone 9 of the gas sensitive layer 7. The coating 18 thus stabilizes the surface of the gas sensitive layer 7.

By means of the coating 18, the sensor signal 19 of the gas sensor 1 essentially corresponds to the target gas concentration 20. It is clearly discernible in FIG. 5 that with a rectangular-shaped gradient of the target gas concentration 20 having a rising slope 21a, 21b and a falling slope 22a, 22b, the sensor signal 19 steeply falls with the rising slope 21a, 21b, and with the subsequent falling 22a, 22b slope, the sensor signal 19 steeply rises back to its level prior to the increase of the target gas concentration 20. The target gas concentration is constant between the rising slope 21a, 21b and the falling slope 22a, 22b. The sensor signal 19 has a more or less constant gradient between the rising slope 21a, 21b and the falling slope 22a, 22b. Furthermore, it can be discerned that the decrease of the sensor signal 19 with a slight increase (in FIG. 5, left) in the target gas concentration 20 is smaller than with a greater increase in the target gas concentration 20 (in FIG. 5, right).

In comparison, FIG. 6 illustrates the gradient of the measurement signal 23 for an analogous gas sensor lacking the coating 18 of the invention. It can be clearly discerned that there is strong interference with the measurement signal 23 during both of the rectangular-shaped gradients of different heights of the target gas concentration 20, and that said measurement signal 23 is deflected downwards once and upwards twice relative to its original level. The analysis of the measurement signal 23 of the prior art gas sensor is therefore considerably more difficult than with the gas sensor 1 of the invention.

The invention claimed is:

1. A gas sensor comprising at least one gas sensitive layer, which has at least one surface zone in which the work function is dependent upon the concentration of a target gas capable of being brought into contact with the surface zone, and further comprising at least one electrical potential sensor capacitatively coupled to the surface zone over an air gap, characterized in that the surface zone of the gas sensitive layer is covered with an electrically insulating coating which is inert to the target gas and which is adhesively bound to the gas sensitive layer and configured so that it is permeable to the target gas and so that it prevents or at least impedes an alteration of the bound state of atoms and/or molecules bound to the surface zone and differing from the target gas when the target gas contacts the surface zone of the gas sensitive layer.

2. The gas sensor as in claim 1, characterized in that the coating is bound to the surface zone of the gas sensitive layer via oxygen bridges.

3. The gas sensor as in claim 1, characterized in that the coating is configured so that it prevents or at least impedes the binding of an electronegative gas differing from the target gas, especially of oxygen, to the surface zone of the gas sensitive layer.

4. The gas sensor as in claim 1, characterized in that the coating is a monomolecular layer.

5. The gas sensor as in claim 1, characterized in that the coating contains a silane, especially one in which a silicon atom is bound to at least one electronegative gas atom, preferably chlorine.

6. The gas sensor as in claim 1, characterized in that the silane has at least one organic residual group.

7. The gas sensor as in claim 1, characterized in that the gas sensitive layer is composed of platinum or palladium.

8. The gas sensor as in claim 1, characterized in that the target gas is a reducing gas, especially hydrogen.

9. The gas sensor as in claim 1, characterized in that the potential sensor is a field-effect transistor, which has a substrate on which a drain and a source are arranged, in that a channel zone is formed between the drain and source, and in that the channel zone is capacitatively coupled to the surface zone of the gas sensitive layer directly over the air gap or indirectly by means of a gate electrode coactive with the channel zone and a sensor electrode conductively connected to the gate electrode.

10. The gas sensor as in claim 1, characterized in that said gas sensor is configured as a Kelvin probe in which the potential sensor is capacitatively coupled to the surface zone of the gas sensitive layer via an electrode separated from the surface zone of the gas sensitive layer by the air gap and capable of being displaced toward and away from said gas sensitive layer.

* * * * *